United States Patent [19]

Lee

[11] 4,419,991
[45] Dec. 13, 1983

[54] SPLINT

[76] Inventor: Roger Lee, 9533 Sunnyside Ave., Ben Lomond, Calif. 95005

[21] Appl. No.: 372,918

[22] Filed: Apr. 29, 1982

[51] Int. Cl.³ .............................................. A61F 5/04
[52] U.S. Cl. .................................................... 128/88
[58] Field of Search ............... 128/88, 80 F, 83, 84 R, 128/84 C, 85, 87 R

[56] References Cited

U.S. PATENT DOCUMENTS

| | | | |
|---|---|---|---|
| 340,971 | 5/1886 | Aloe | 128/88 |
| 1,340,630 | 5/1920 | Maddox | 128/88 |
| 2,007,127 | 7/1935 | Longfellow | 128/85 |
| 2,052,990 | 9/1936 | Siebrandt | 128/85 |
| 2,252,607 | 8/1941 | Baker | 128/85 |
| 2,926,662 | 3/1960 | Pile | 128/88 |
| 3,417,748 | 12/1968 | Bimler | 128/85 |
| 3,454,002 | 7/1969 | Westlake et al. | 128/87 R |
| 3,477,428 | 11/1969 | Hare | 128/85 |
| 3,848,589 | 11/1974 | Throner | 128/84 C |
| 3,906,942 | 9/1975 | Lumb, Jr. et al. | 128/84 C |
| 4,005,705 | 2/1977 | Short et al. | 128/87 R |
| 4,054,130 | 10/1977 | Franke | 128/87 R |
| 4,174,709 | 11/1979 | Maddux | 128/85 |
| 4,336,796 | 6/1982 | Andrews et al. | 128/87 R |

FOREIGN PATENT DOCUMENTS 1124633   3/1962   Fed. Rep. of Germany .... 128/80 F

Primary Examiner—John D. Yasko
Attorney, Agent, or Firm—Jack M. Wiseman

[57] ABSTRACT

A splint includes upper and lower generally planar limb support sections, and means for adjustably connecting the sections so that one seciton can be adjusted to a position inclined upwardly or downwardly relative to the other section, or can be moved to a position extending laterally at an angle away from the other section, or can be adjusted to a position involving both up and down and lateral movement of the sections.

7 Claims, 8 Drawing Figures

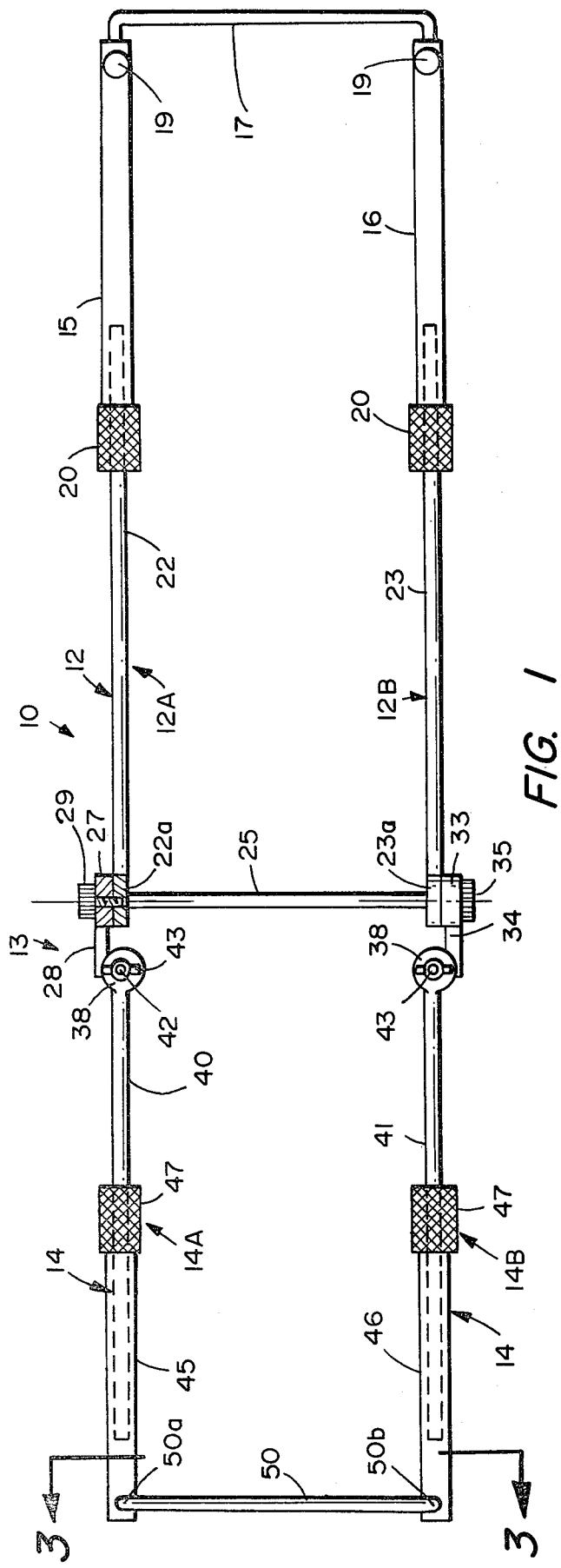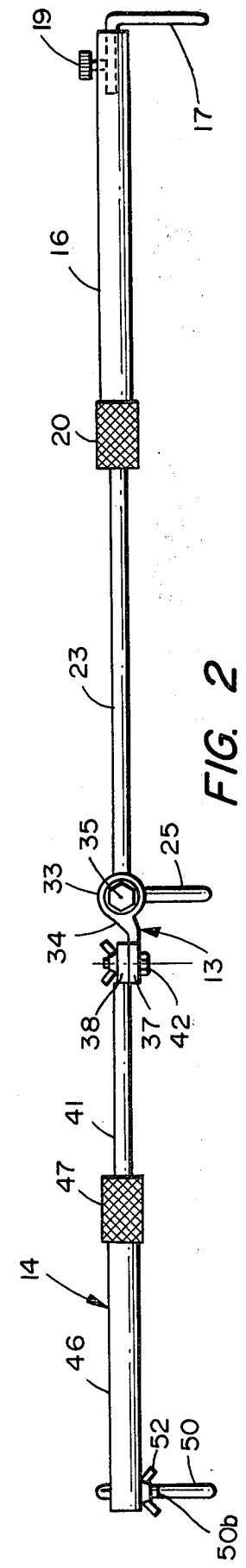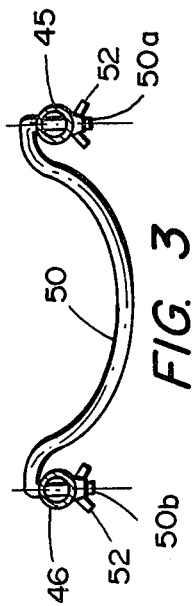

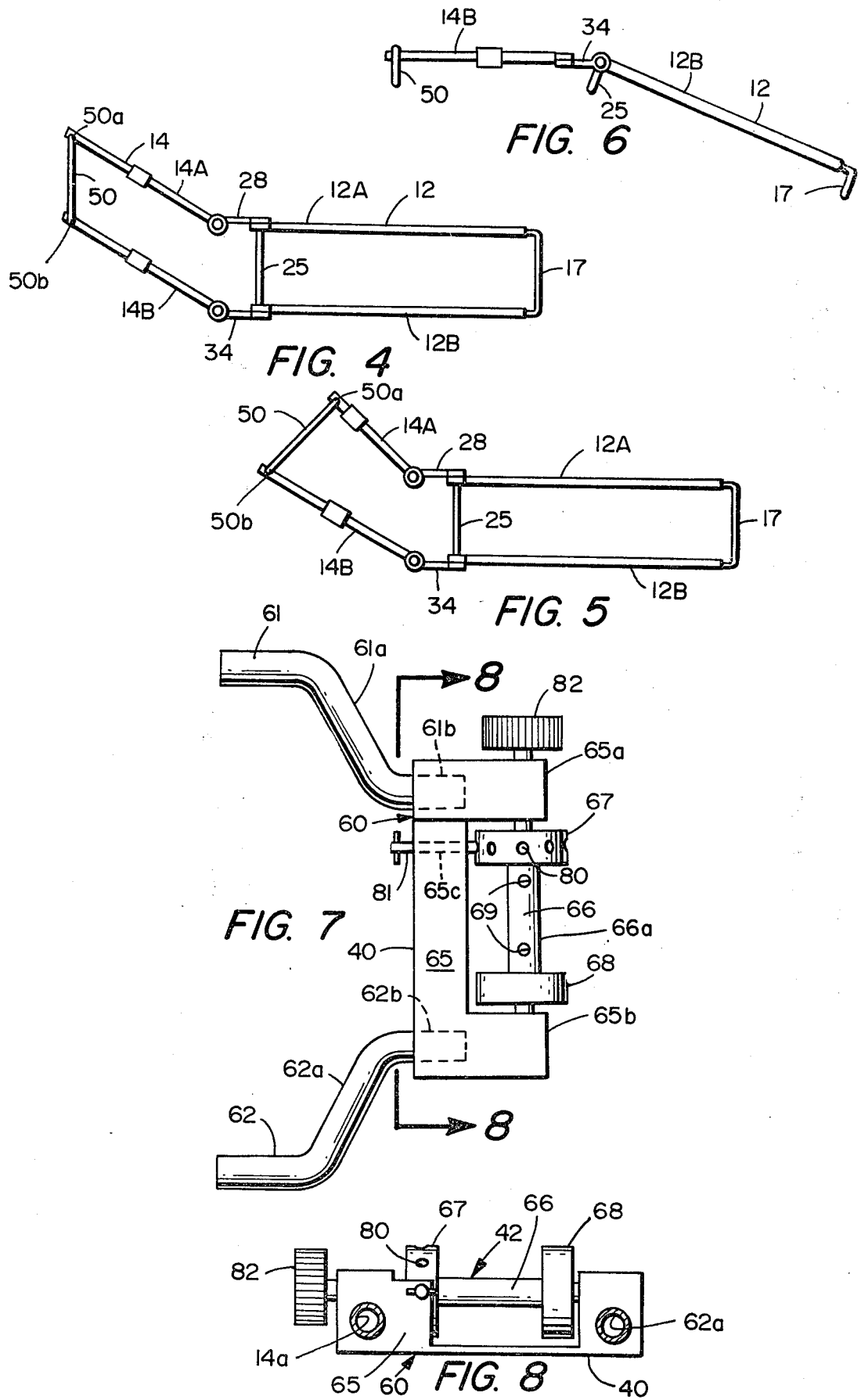

SPLINT

BACKGROUND OF THE INVENTION

This invention relates to splints used for temporarily supporting an injured limb, and more particularly concerns a splint having an improved articulated construction.

Splints have been used for many years at the site of an accident for immobilizing injured arms and legs. These conventional splints typically have pivotally interconnected, generally planar sections that can be adjusted relative to each other so that the plane of one section may be inclined relative to the plane of the other section. The patents to Throner, U.S. Pat. Nos. 3,848,589, to Aloe, 340,971, and Siebrandt, 2,052,990 disclose such splints. The ability of the splint to pivot makes it possible to accommodate a limb that is bent in one direction. However, it often happens that a compound break is experienced and the injured limb has sections oriented in more than two directions. Since it is desirable from the viewpoint of the examining doctor that the injury be immobilized in the position that it assumed at the time it was discovered, various techniques have been used to obtain this result. These techniques included the use of an assortment of various cardboard splints, pillows, sand bags and the like. Applying the cardboard splints not only cause considerable movement of the injured member but, in addition, they did not provide adequate support. Similarly, the use of sand bags and pillows provide inadequate support.

Accordingly, it is an object of the present invention to provide a splint that can be applied quickly and easily to a member that has undergone a compound break and which will provide adequate support for the member in its dislocated condition.

SUMMARY OF THE INVENTION

A splint includes two sections that are connected by a two direction hinge so that the sections can be adjusted up and down and sidewise relative to each other.

DESCRIPTION OF THE DRAWINGS

FIG. 1 is a diagrammatic plan of one embodiment of the splint of the present invention.

FIG. 2 is a diagrammatic side elevation of the splint of FIG. 1.

FIG. 3 is a diagrammatic section taken along line 3—3 of FIG. 1.

FIGS. 4, 5 and 6 are schematic showings of the splint of FIG. 1, illustrating various adjusted positions of the members of the splint.

FIG. 7 is a fragmentary diagrammatic view of a second embodiment of the splint of the present invention.

FIG. 8 is a section taken along line 8—8 of FIG. 7.

DESCRIPTION OF A PREFERRED EMBODIMENT

In FIG. 1 the reference numeral 10 indicates generally a splint which comprises a lower section 12, an intermediate section 13, and an upper section 14. Section 12 includes a pair of aluminum tubes 15 and 16 connected at their end by a cross-brace 17 which has a generally concave, cradle-like configuration at its central section and has inturned ends, each of which is disposed in the open end of one of the tubes 15 or 16 and locked therein by a set-screw 19 (FIG. 2) that is threaded through a tapped hole near the end of the associated tube.

A cylindrical knurled nut 20 is threaded on the free end of each of the tubes 15 and 16. The portion of each tube underlying the nut 20 is longitudinally slotted, and the threads on that slotted end are arranged so that, when the nut 20 is rotated in a particular direction, the end of the tube is collapsed to engage an end portion of one of two solid steel rods 22 or 23 that are telescoped into the ends of the tubes 15 and 16 respectively. When the nuts are tightened on the tubes 15 and 16, the tube 15 and the rod 22 form a rigid side member identified by the numeral 12A, and the tube 16 and the rod 23 form a rigid side member identified as 12B. The rod 22 has an enlarged circular plate 22a formed at one end and the rod 23 has an enlarged circular plate 23a formed at its end. A second cross-brace 25, which has a downwardly-offset concave central section, extends between and is welded to the plates 22a and 23a. Thus, when the nuts 20 are tightened on the tubes 15 and 16, and the set-screws 19 have been screwed down to lock the cross-brace 17 in place, the lower section 12 of the splint is a rigid, unitary member.

The intermediate section 13 of the splint includes two spaced rigid arms 28 and 34 which are identical, only oppositely disposed. Arm 34 has a circular plate 33 formed at one end and a circular plate 37 (FIG. 2) formed at its other end, plate 33 being disposed in a plane that is at right angles to the plane of plate 37. Similarly, arm 28 has a plate 27 at one end and a and a plate 37 (not shown) at its other end that is identical to plate 37 of arm 34 and is at right angles to plate 27. The lower section 12 of the splint is releasably secured to the intermediate section 13 by screws 29 and 35. Screw 29 extends freely through an opening in the plate 27 and is threaded into a tapped hole in the circular plate 22A. Similarly, screw 35 releasably secures plate 23a of section 12 to arm 34 of section 13.

The upper section 14 of the splint includes two spaced rods 40 and 41, each of which has an annular plate 38 formed at one end. A bolt 42 that extends through aligned holes in each pair of abutting circular plates 37 and 38, receives a wing nut 43 to lock the plates in non-slip relation.

Each of the rods 40 and 41 extends into the threaded, slotted end of an aluminum tube 45 or 46. A cylindrical nut 47 is threaded on the threaded end of each of the tubes 45 or 46 and is arranged to press that end down into tight frictional engagement with the associated rod 40 or 41 to form rigid side members 14A and 14B. The free ends of the two tubes 45 and 46 are connected together by a cross-brace 50 which, as seen in FIG. 3, has a concave central portion, similar to the central portions of cross-braces 17 and 25, and downturned threaded ends 50a and 50b, each of which is adapted to receive a wing nut 52, the nuts being effective to press the tubes 45 and 46 into tight engagement with the cross-brace 50.

In FIGS. 4, 5 and 6 some of the possible adjusted positions of the members of the splint are diagrammatically indicated. The adjustments will be explained with reference to an initial position, shown in FIGS. 1 and 2, in which all three sections 12, 13 and 14 are substantailly in the same plane, the side members 45, 40, 28, 22 and 15 are in general alignment, and the side members 46, 41, 34, 23 and 16 are in general alignment.

If the two wing nuts 52 at the upper end of the splint are loosened to permit pivoting of the cross-brace 50 relative to the side members 14A and 14B, and the wing nuts 43 at the intermediate section are backed-off to permit pivoting of the side members 14A and 14B relative to the arms 28 and 34, respectively, of the intermediate section 13, the side members 14A and 14B can be moved to a position out of alignment with the side members 28 and 34 respectively as shown in FIG. 4.

Also, starting with the FIG. 1 position, if the screws 29 and 35 are loosened, lower section 12 can be pivoted downwardly, as shown in FIG. 6, or upwardly out of the plane of sections 13 and 14, as seen in FIG. 6.

Similarly, starting from the FIG. 1 position, if all four of the wing nuts 52 and 43, and the screws 29 and 35 are loosened, the lower section 12 can be pivoted downwardly or upwardly relative to the intermediate section 13 while the side members 14A and 14B of section 14 can be pivoted laterally relative to the intermediate section 13 to a variety of positions. Thus, positions which are combinations of the positions of FIGS. 4 and 6 can be attained.

Since the rods 40 and 41 of upper section 14 are telescoped in the ends of the tubes 45 and 46, respectively, the length of each of the side member 14A and 14B may be varied independently of the length of the other member. When one side member is longer than the other, a position can be attained wherein the upper section 14 is pivoted at a rather acute angle away from the longitudinal centerline of the lower section 12, as shown in FIG. 5.

It will therefore be apparent that the intermediate section 13 of the splint acts as a duo-directional joint that permits the lower section 12 to move from a position of generally planar and longitudinal alignment with upper section 14 to a position wherein the plane of section 12 is inclined relative to the plane of section 12 and in which section 14 slants away from intermediate section 13.

In FIGS. 7 and 8 a second embodiment of the splint of the present invention is illustrated. In this embodiment a traction unit 60 is provided with tubular side members 61 and 62 that are telescoped into the ends of tubes 15 and 16 of the lower section 12, instead of the ends 17a and 17b of the cross-brace 17 of FIG. 1. Thus, in the embodiment of FIGS. 7–8, the traction unit 60 replaces the cross-brace 17. All of the members of this embodiment are identical to the members of the splint of FIGS. 1 and 2 except the parts shown in FIGS. 7 and 8 and reference may be had to the description of the embodiment of FIGS. 1 and 2 for a complete description of the embodiment of FIGS. 7 and 8.

The side members 61 and 62 are locked in the tubes 15 and 16 by the setscrews 19, and are provided with inwardly slanted portions 61a and 62a longitudinally-extending end portions 61b and 62b respectively which are secured, as by a press fit, in a rigid transverse block 65. The block 65 has two spaced wings 65a and 65b which rotatably journal a shaft 66 on which two guide wheels 67 and 68 are keyed. Wheel 67 is provided with a plurality of radially oriented cylindrical sockets 80 spaced equi-angularly around the periphery of the wheel and a pin 81, which is slidably journalled in a passage 65c in the block 65, is arranged to be selectively inserted in one of the sockets 80 to lock the shaft against further rotation. A knurled handwheel 82 is keyed to the shaft to facilitate rotation of the shaft by a user of the traction unit to apply tension to an injured limb.

The traction unit includes a pair of belts (not shown) which have end portions that carry ringlets. When a collar at the other ends of the belts is disposed around an injured member, the ends of the belts that carry the ringlets extend away from the injured member and the ringlets are adapted to be hooked over a hook carried by a belt section that is secured to an enlarged diameter portion 66a of the shaft 66 between the guide wheels 67 and 68 by a plurality of screws 69. Other devices may be used such as the angle-engaging tape shown in the patent to Hare, U.S. Pat. No. 3,477,428 or the cuff disclosed in the patent to Lumb et al., U.S. Pat. No. 3,906,942, that are adapted to engage an injured limb and transmit a pulling force to the limb as the handwheel 82, with pin 81 withdrawn from the wheel 67, is rotated and the section of the belt is wrapped around the shaft 66. When the limb has been put under the desired amount of tension, the pin 81 is slid into the hold 80 on wheel 67 that is in alignment with the passage 65c in the block 65 to arrest the shaft in the belt-tensioned position.

In one arrangement of the splint of FIG. 1, the splint is approximately ten inches wide, the lower section 14 is approximately twenty inches long, section 13 is approximately twenty-four inches long, and upper section 12 is approximately twenty-four inches in length. Since the splint is longitudinally adjustable, it can be arranged to fit the legs of children or adults, as well as an adult arm. Since it is light in weight, it is easily maneuvered and can be applied quickly and easily to the top, bottom, inside or outside of the victim's arm or leg even before extrication of the victim from a wrecked vehicle, thus assuring immobilization during the extrication procedure. Most importantly, the ability of the sections of the splint to assume various relative positions assures that the injured area stays open and available for medical treatment.

Straps (not shown) are secured to and extend transversely between the side members of the sections 12, 13 and 14 of the splint at spaced intervals for the purpose of holding the injured limb in position relative to the splint. These straps are provided with Velcro end portions to facilitate the anchoring of the limb to the splint, and these straps may also be used to secure pressure dressings in place.

From the foregoing description it will be apparent that the present invention provides a unique, versatile splint that can be quickly and easily applied to an injured limb to immobilize the limb in a position which accommodates any angulation of the members of the limb resulting from an accident.

I claim:

1. A splint comprising first and second limb-support sections, and a plurality of transversely spaced articulated joints connecting said sections for pivotal adjustment in directions to move one section from a position of general longitudinal and planar alignment with the other section to a position wherein the plane of one section is inclined relative to the plane of the other section and said one section is slanted away from longitudinal alignment with said other section, said articulated joints comprising a plurality of transversely spaced arms connected for pivotal adjustment at one end to said one section and connected for pivotal movement at the other end to said other section, a pivot axis between each arm and said one section being at right angles to and spaced from a pivot axis between the same arm and said other section.

2. The splint of claim 1 wherein said one support section comprises three elongate members that form three sides of a parallelogram linkage with each of the parallel side members thereof being connected at one end to the cross member of the parallelogram linkage and at the opposite end to the other end of one of the spaced arm of said articulated joints.

3. The splint of claim 2 wherein each of said joints connecting said spaced arms to said first and second limb-support sections includes a threaded member and a wing nut disposed on said threaded member, said other limb-support section comprising side members and a cross-brace connected to said side members of said other limb-support section at the ends thereof opposite from which said spaced arms are connected.

4. The splint of claim 2 wherein said other section comprises a rigid rectangular frame and each of said spaced arms is connected respectively for pivotal adjustment to one side member of said rectangular frame.

5. The splint of claim 1 further comprising a traction unit, and mounting means for securing said traction unit on an end portion of said one section.

6. The splint of claim 5 wherein said other section includes a pair of spaced longitudinally-extending side members and said traction unit includes a block connected transversely between end portions of said side members, a shaft rotatable in said block, means for securing an end of a traction belt to said shaft for rotation with said shaft whereby rotation of said shaft winds the end of the belt around the shaft and tensions the belt, and a pin slidable in a passage in said block and engageable with said shaft to prevent rotation of the shaft when the belt is tensioned.

7. The splint of claim 2 wherein said other limb-support section comprises side members and a cross-brace connected to said side members of said other limb-support section at the ends thereof opposite from which said spaced arms are connected.

* * * * *

UNITED STATES PATENT AND TRADEMARK OFFICE
CERTIFICATE OF CORRECTION

PATENT NO. : 4,419,991

DATED : December 13, 1983

INVENTOR(S) : Roger Lee

It is certified that error appears in the above-indentified patent and that said Letters Patent is hereby corrected as shown below:

Column 6, line 3, change "one" to --other--.

Signed and Sealed this

Seventeenth Day of May, 1994

Attest:

BRUCE LEHMAN

*Attesting Officer*     *Commissioner of Patents and Trademarks*